United States Patent [19]

Middlebrook et al.

[11] 3,948,729

[45] Apr. 6, 1976

[54] ASSAY OF GENTAMICIN IN BLOOD

[75] Inventors: Gardner Middlebrook; W. D. Tigertt, both of Baltimore, Md.

[73] Assignee: Johnston Laboratories, Inc., Cockeysville, Md.

[22] Filed: Mar. 18, 1974

[21] Appl. No.: 452,264

[52] U.S. Cl. ............................................ 195/103.5 R
[51] Int. Cl.² ..................... G01N 33/16; G01T 1/16
[58] Field of Search ................................... 195/103.5

[56] References Cited
UNITED STATES PATENTS 3,676,679  7/1972  Waters............................ 195/127 X

OTHER PUBLICATIONS

Noone et al., Lancet, 2(7714), July 3, 1971, pp. 16–19.
Bersaques, Liquid Scintillation Counting, Vol. 3, "A Micromethod for Urease," 303–306, (1973).
McDonald et al., Enzymologia, Vol. 42, (1972), pp. 1–9.

Chemical Abstracts, 78:93000y.

*Primary Examiner*—A. Louis Monacell
*Assistant Examiner*—Esther L. Massung
*Attorney, Agent, or Firm*—Schuyler, Birch, Swindler, McKie & Beckett

[57] ABSTRACT

The ability of gentamicin to inhibit urease synthesis by a gentamicin susceptible strain of an adaptive urease producing microorganism is employed to provide an assay for the concentration of gentamicin present in the blood of a patient being treated with gentamicin. The gentamicin concentration in the liquid portion of blood is determined by comparing the amount of $C^{14}O_2$ produced by a gentamicin susceptible strain of an adaptive urease producing microorganism from a culture medium containing an aliquot of blood test sample and a measured amount of $C^{14}$ urea with the $C^{14}O_2$ produced by that microorganism from controls using known concentrations of gentamicin in blood samples.

9 Claims, 1 Drawing Figure

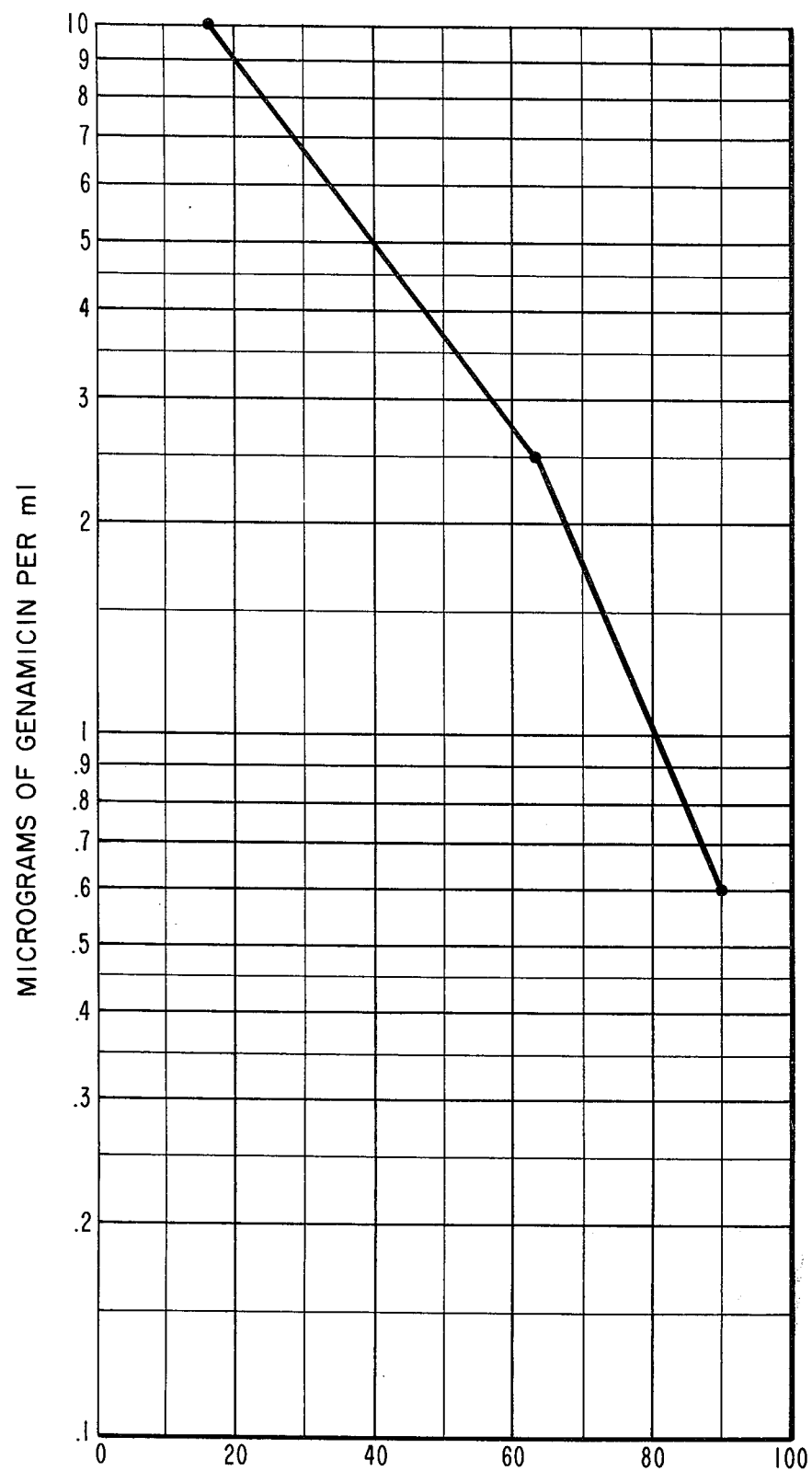

ASSAY OF GENTAMICIN IN BLOOD

DESCRIPTION OF THE INVENTION

This invention relates to the assay of gentamicin in blood.

Gentamicin is an antibiotic of the aminoglycoside class which has proved to be very useful for the treatment of life-threatening infections, particularly septicemia or urinary tract infections due to gram-negative bacteria. Gentamicin must be used with care, however, because it has a low therapeutic index; that is, the ratio of its minimal toxic dose to its effective antibacterial dose is low. Therefore, there is a need for a rapid assay of its concentration in patients under treatment with gentamicin in order to monitor treatment so that the gentamicin level will neither be too low for chemotherapeutic effectiveness nor so high as to risk toxic signs or symptoms in the patient.

Five different methods have been described for the assay of gentamicin: (1) agar diffusion, e.g., Antimicrobial Agents and Chemotherapy, 4 No. 5, Nov. 1973, pp. 569–73; Ibid, 1970, pp. 83–90; (2) tube dilution, e.g., J. Biol. Chem., 144, pp. 285–6; (3) pH change, e.g., Laucet, Aug. 17, 1968, pp. 375–8, Ibid, July 3, 1971, pp. 16–18, Ibid, Dec. 2, 1972, pp. 1194–5; Ibid, Jan. 6. 1973, pp. 49–50; Ibid, Feb. 10, 1973, pp. 315–17; (4) enzymatic assay of adenylation or acetylation; e.g., New England Journal of Medicine, 286, No. 11, 1972, pp. 583–6; and (5) radioimmune method, e.g., Nature New Biology, 239, Oct. 18, 1972, pp. 214–6. The first two of these require at least 4 hours for their performance. The third, inter alia, requires a large number of tubes, a good deal of laboratory effort and a minimum of 90 minutes for its performance. The last two require a scintillation counter which is expensive and which is available in few hospital laboratories.

It is one object of this invention to provide a method for the rapid assay of gentamicin in the blood of human beings.

It is another object of this invention to provide a rapid assay of gentamicin in the blood of human beings that entails a minimum of processing.

It is an additional object of this invention to provide an assay of gentamicin in the blood of human beings that may be accomplished by a laboratory technician without the use of special expertise.

In one embodiment of this invention there is provided a method of determining the level of gentamicin in blood plasma which comprises:

a. Incubating a gentamicin susceptible strain of an adaptive urease producing microorganism in a liquid medium in a closed container having gas space over the medium, said medium containing an aliquot of the liquid portion of blood from a patient being treated with gentamicin and a measured amount of $C^{14}$ urea;

b. Determining the amount of $C^{14}O_2$ in the gas space in said container after said incubation; and c. Comparing said amount of $C^{14}O_2$ with that produced from control media containing an aliquot of the liquid portion of blood with known concentrations of gentamicin processed in the same manner, as specified by steps (a) and (b) above.

In another embodiment of this invention there is provided a method of determining the level of gentamicin in blood which comprises:

a. Incubating a gentamicin susceptible strain of an adaptive urease producing microorganism in a liquid medium containing urea and an aliquot of the liquid portion of blood from a patient being treated with gentamicin;

b. Adding a measured amount of $C^{14}$ urea to said medium after an initial period of incubation;

c. Further incubating said culture in a closed container having a gas space over the liquid medium at a temperature at which further urease synthesis is interrupted but at which preformed urease activity is enhanced;

d. Determining the amount of $C^{14}O_2$ in the gas space in said container after said incubation; and e. Comparing said amount of $C^{14}O_2$ with that produced from control media containing an aliquot of the liquid portion of blood with known concentrations of gentamicin processed in the same manner, as specified in steps (a) through (d) above.

The assay of this invention is based upon the known ability of gentamicin to inhibit the adaptive synthesis of the enzyme urease by a test strain of gentamicin susceptible microorganism in culture in vitro. Urease breaks down urea into ammonia and carbon dioxide ($CO_2$) and it has now been determined that, by adding a known amount of $C^{14}$ urea to the medium, the amount of $C^{14}O_2$ liberated from the medium may be employed as a basis for a rapid and reliable assay of gentamicin.

A gentamicin susceptible strain of an adaptive urease producing microorganism is incubated in a medium containing an aliquot of the blood sample to be assayed and the gentamicin present in the sample will depress the amount of urease produced by the strain in relation to the concentration of the gentamicin present in the sample. By employing $C^{14}$ urea as an additive to the media, it is possible to determine the amount of $C^{14}O_2$ liberated from the medium and to use this as a measure of the urease produced by the strain which, in turn, is an indication of the amount of gentamicin present in the sample. Controls are run with pooled samples of the liquid portion of normal blood containing known concentrations of gentamicin and the $C^{14}O_2$ liberated from these are also measured. The controls containing larger concentrations of gentamicin provide smaller amounts of $C^{14}O_2$ because of greater inhibition of urease synthesis by the test strain. By comparing the amount of $C^{14}O_2$ given off in the test assay with the $C^{14}O_2$ given off by the controls, the concentration of gentamicin in the test sample readily can be determined.

The assay of this invention is useful when commencing treatment with gentamicin and is also useful in monitoring the level of gentamicin in the blood during the period of treatment.

In one embodiment of this invention a culture of gentamicin susceptible strain of adaptive urease producing microorganism is inoculated into a medium containing an aliquot of the liquid portion of blood from a patient being treated with gentamicin, a known amount of $C^{14}$ urea, and cultured for a given period of time before the $C^{14}O_2$ liberated from the medium is measured and compared against controls similarly processed. This procedure can be accomplished in a short period of time and provides a practical assay of gentamicin in the test blood plasma sample.

In another embodiment of this invention an even more accurate assay of gentamicin is provided. In this embodiment the strain of microorganism is incubated for a period of time in a culture medium containing urea and an aliquot of the liquid portion of blood from a patient being treated with gentamicin; $C^{14}$ urea is then added to the culture medium and the sample is incubated for an additional period of time at a somewhat elevated temperature which inhibits further urease production by the microorganism but enhances the activity of the urease already formed. After this second incubation period, the $C^{14}O_2$ liberated from the culture is measured and compared against controls similarly processed. Tests have determined that this procedure provides an assay that on replicate assays will not vary more than about ±10%.

If desired, replicates may be employed in the assay of this invention but it appears that this assay is sufficiently reliable that replicates need not be used.

The liquid blood portion employed in the assay of this invention should be essentially free of red blood cells. Either blood plasma, prepared by centrifuging blood, or blood serum, prepared by coagulating blood, readily may be employed. If plasma is used, it desirably will contain an anti-coagulant such as heparin. The amount of blood plasma or serum to be added to the medium generally will range from about 2.5 to 10% by volume with amounts of from about 4 to about 6% being preferred. If blood plasma is used for the test, plasma should also be used for the controls; similarly, if serum is used for the test it should also be used for the controls.

The strain of microorganism to be used in the assay of this invention is a gentamicin susceptible strain of an adaptive urease producing microorganism and readily may be obtained by one skilled in the art. By "gentamicin susceptible" is meant a microorganism that, in the Kirby-Bauer standard assay with Mueller-Hinton medium, provides a zone of inhibition of at least 18 mm about a disc containing 10 mcg of gentamicin after 15 hours incubation (e.g., overnight) at 35°–37°C. Such procedure is described, inter alia, in American Journal of Clinical Pathology, 45, No. 4, 1966, pp. 493–6; and Federal Register 37 (191), 20527–20529 (1972). An adaptive urease producing microorganism is one that (a) produces no detectable urease activity in a culture grown in the absence of urea, but (b) upon inoculation of about $10^8$ viable units of microorganism into 1.0 ml of tryptic soy broth containing 1% urea will decompose at least 200 mcg of urea during a 1 hour incubation at a pH of 7.5–8.5 and at a temperature of 35°–37°C. Preferred strains for the practice of this invention are of the genus Proteus and particularly preferred strains are of the species *Proteus mirabilis*. Strains useable in the practice of this invention are known and one such strain is deposited as A. T. C. C. No. 31008. (TM 101).

In order to obtain uniform inoculation of test samples and controls, a strain of gentamicin susceptible microorganism may be grown in tryptic soy broth or the like which, of course, should be free of urea, and culture then divided into small portions which in turn are employed to inoculate the media in the assay of this invention. Such portions may be preserved at low temperature (e.g., −70°C) for considerable periods of time and thawed and used as needed. The number of viable microorganisms to be added to the medium will generally range from about $5 \times 10^6$ to about $5 \times 10^7$. Freeze drying (e.g., lyophilization) should be employed with caution, if at all, because such technique tends to provide a considerable number of dead cells at the time of inoculation and these cells bind gentamicin and reduce the level of sensitivity of the assay.

So long as inoculum portions from a single inoculum work-up are available, it is not necessary to rerun controls each time blood plasma from a different patient is tested. Rather, controls can be conducted and the tests which are performed thereafter employing inoculum from that culture work-up can be compared to the data from the controls.

The choice of a culture medium is within the skill of the routineer. A typical medium will contain a carbohydrate and a nitrogen source. The carbohydrate may be glucose, fructose, galactose, xylose or the like, while the nitrogen source may be any assimilable nitrogen, including amino acids, nitrates, nitrites or the like. At least some urea should be present in the medium. Desirably the medium will contain at least about 0.1% urea by weight and preferably at least about 0.5% urea. Generally about 1% urea provides very good results but amounts up to about 2% may be employed. If a single incubation is to be employed, it is not necessary that all urea present be radioactive, only a portion need be $C^{14}$ urea. In the second embodiment of this invention the above levels of urea will be free of $C^{14}$ urea since the $C^{14}$ urea is added only for the second portion of the process.

A variety of calcium, potassium, and magnesium salts also may be employed in the medium including the chlorides, sulfates, phosphates, and the like. Similarly, phosphate and sulfate ions can be supplied as any of a variety of salts. While salts which supply both the desired anion and cation may be employed (e.g., potassium phosphate, magnesium sulfate) the selection is by no means so limited. Again, such materials are conventional in media and the selection of specific materials as well as their proportion is within the skill of the routineer.

The so-called "minor elements" are commonly understood to include manganese, iron, zinc, cobalt, and possibly others. Trace quantities thereof are preferred, and such quantities are commonly present in the materials used in the preparation of media.

Finally, the medium may contain a buffer to maintain the pH in the desired range. Once more a wide variety of materials may be utilized. Potassium or ammonium phosphates often are employed to maintain the pH of media.

$C^{14}$ urea is commercially available and is most conveniently used in the practice of this invention as a solution in distilled or deionized water. If an initial incubation step is employed before the $C^{14}$ urea is added to the solution, an agent such as sodium azide may be added with the $C^{14}$ urea to prevent contamination of the solution in the latter portion of the process. The amount of $C^{14}$ urea added to the assay medium is a matter of choice. Generally, the $C^{14}$ urea addition will provide from about 0.5 to about 5 $\mu$Ci per 4 ml of medium with about 1 $\mu$Ci per 4 ml of medium being a preferred level of addition.

The assay medium need not be freshly mixed at the time of each assay but may be made up in advance. Containers with medium are preferably maintained at relatively low temperatures, e.g., 2°–8°C or lower. Since the $C^{14}$ urea may tend to decompose, that ingredient is generally added at the time of the assay.

At least the portion of the assay following addition of $C^{14}$ urea to the medium is conducted in a closed container having a gas space over the medium. Desirably the gas space will comprise at least about 25% of the total volume of the container but this may vary widely and containers having 90% or more gas space readily may be employed. The allocation of medium volume and gas volume within a container is not critical as long as sufficient gas space exists to provide oxygen needed for incubation of the culture and to provide space for the collection of gaseous $C^{14}O_2$. Once again this choice is within the skill of the art. The container will also desirably include a closure member made of rubber, plastic or the like that will permit access to the container with hypodermic needles and the like so that materials can be added and gas can be withdrawn without otherwise disturbing the seal.

The test microorganism is grown by inoculating the assay medium with the culture and incubating the medium at a temperature suitable for growth and generally at from about 35° to about 40°C. Once again an appropriate growth temperature for any given microorganism can readily be determined by one skilled in the art. Optimum temperature for growth of Proteus mirabilis, for example, is approximately 37°C and incubation at or near that temperature provides most rapid growth. It has been determined that incubation for 1 hour is satisfactory for the assay of this invention. Other incubation temperatures may, of course, be employed but the incubation time will tend to be longer. While agitation during incubation has been determined to be unnecessary, it may be employed if desired.

In the embodiment of this invention wherein a second incubation is utilized, that second incubation is desirably carried out at a somewhat elevated temperature of about 50°C to about 60°C, sufficient to depress further synthesis of urease by the microorganism while at the same time enhancing the activity of the urease previously produced. Incubation for about 15 minutes has been found to be satisfactory for this step.

Following incubation at the elevated temperature, the $C^{14}O_2$ in the gas space is measured. The measurement may be taken immediately, taking care that the temperature of the samples and controls are the same. Preferably, all samples are at room temperature when the $C^{14}O_2$ measurement is made but any temperature can be employed so long as both the controls and samples are at the same temperature when measured.

At the end of the incubation, it is desirable to acidify the medium with sulfuric acid, hydrochloric acid, acetic acid or the like to a pH of not greater than about 2 to terminate any further enzymatic activity and to decompose any bicarbonate that is formed. Such step favors liberation of $CO_2$ from the liquid medium and release of $CO_2$ can be further enhanced by agitating or swirling the medium. In the event the medium is agitated or swirled, it desirably should contain an antifoaming agent. Such agents are commonly used in fermentations and are described, inter alia, in Process Biochemistry, Oct. 1967, pp. 47–8.

The $C^{14}O_2$ liberated from the test culture can be measured by a variety of methods, including those described, inter alia, in Levin U.S. Pat. No. 2,914,447, American Journal of Public Health 54, 827–833 and 834–844 (May 1964), and Chemical and Engineering News 39 45, 44–45 (Nov. 6, 1961). Preferably, however, the $C^{14}O_2$ is measured while in the gaseous state employing a method and apparatus described, inter alia, in Waters U.S. Pat. No. 3,676,679 which is incorporated herein by reference. In that method at least a portion of the gaseous atmosphere is removed from the container and the amount of $C^{14}O_2$ is measured while in a gaseous state in an ionization chamber. A commercial instrument is available for that procedure under the trade name "BACTEC" (Johnston Laboratories, Inc.) and provides a reading of 0 to 100. The use of such procedure shortens and greatly facilitates the assay. Indeed, several samples may be analyzed for $C^{14}O_2$ seriatim.

Three controls (one low, one intermediate and one high gentamicin concentration) are sufficient to establish a standard curve. Controls employing gentamicin concentrations of 0.6 mcg, 2.5 mcg and 10 mcg per ml have been found to be satisfactory to establish a useable curve over the entire range but controls varying about ±25% from these values may be employed if desired. These are particularly apt controls since a minimum treatment level with gentamicin is generally considered to be approximately 1 mcg/ml while the maximum treatment level is generally considered to be about 10 mcg/ml with any concentration over about 10 mcg/ml constituting a potential hazard to the patient.

The control results may be graphed on two-cycle semi-log paper with the log scale as ordinate. The abscissa is divided into 100 units corresponding to the Bactec galvanometer scale of units, and gentamicin concentrations constitute the ordinate (logarithmic). The points for the low, intermediate and high concentrations of gentamicin are plotted and connected by two straight lines as shown on the accompanying graph (FIG. 1). Studies have shown that values of gentamicin between the low concentration (e.g., 0.6 mcg/ml) and intermediate concentration (e.g., 2.5 mcg/ml) lie on or very close to the straight line between these two points; and the same has been shown to be true for gentamicin values between the intermediate and high concentration (e.g., 10 mcg/ml) of gentamicin.

It will be apparent that more than three controls may be run if desired. Similarly other graphs, a computer, formula, or the like may be employed for the comparison of the test sample with the controls. Generally, however, it is necessary to run at least three controls, one at a relatively low gentamicin concentration, one at an intermediate concentration, and one at a relatively high concentration.

In order to provide a fuller understanding of the invention, a detailed description of a typical procedure according to each of the embodiments of this invention and employing *Proteus mirabilis* will now be described.

A culture of *Proteus mirabilis* is grown over night in tryptic soy broth at pH 7.8 and at 37°C. The culture is then divided into 3.0 ml lots in sterile disposable plastic tubes, frozen and stored at −70°C. These tubes provide the inoculum for the assays.

A typical sterile culture medium contains 0.2% glucose, 0.1% casein amino acids, 1% urea, tris-(hydroxymethyl) - aminomethane buffer 0.021M (hereafter reffered to as tris buffer) and exhibits a pH of 8.4.

The *Proteus mirabilis* inoculum is thawed at room temperature and used immediately. Into 20 ml serum bottles with a rubber septum top, 3.0 ml of culture medium, 0.4 ml of *Proteus mirabilis* inoculum, 0.2 ml of the test blood plasma, and 1 ml of $C^{14}$ urea (1.0 µCi/ml) are added. Additions need not be made asceptically. The mixture is incubated at about 37°C for 1 hour and thereafter the $C^{14}O_2$ in the air space is measured at room temperature on a Bactec instrument.

Three controls are conducted as described above except that pooled normal human blood plasma containing 0.6 mcg, 2.5 mcg, and 10 mcg gentamicin are employed instead of the test blood plasma sample. The gaseous $C^{14}O_2$ measurements from these controls are plotted on two-cycle semi-log paper with the log scale as ordinate. The points for 0.6, 2.5 and 10 mcg of gentamicin per ml are plotted and connected by two straight lines (i.e., 0.6 point is connected to 2.5 point and 2.5 point is connected to 10 point). The test $C^{14}O_2$ reading is then compared to the graph which indicates the concentration of gentamicin in the test sample that provides such $C^{14}O_2$ reading.

In the practice of another embodiment of the invention, the *Proteus mirabilis* inoculum, prepared as above, is thawed and 0.4 ml of the inoculum is added to 20 ml serum bottles with a rubber septum top containing 3.0 ml of the culture medium described above, together with 0.2 ml of the test blood plasma. Following incubation at 37°C for 1 hour, 1.0 ml of $C^{14}$ urea is added and the contents are well mixed and incubated at 56°C for 15 minutes. At this temperature further synthesis of urease is essentially terminated but the preformed urease activity is enhanced. After the incubation at 56°C the mixture is cooled, preferably quickly, and 0.2 ml of anti-foam agent (e.g., decyl alcohol) is then added and the mixture is again thoroughly mixed. Following addition of an anti-foam agent, 1.0 ml of a reaction terminator (e.g., 2N sulphuric acid) is added and the mixture is well mixed and is then swirled to remove all bubbles. If desired, the anti-foam agent and the reaction terminated can be added at the same time and even in the same solution. The reaction terminator serves to terminate further enzymatic activities and release $CO_2$. The containers at room temperature are then measured for $C^{14}O_2$ with a Bactec instrument.

Three controls are conducted as described above except that pooled normal human blood plasma containing 0.6 mcg, 2.5 mcg, and 10 mcg per ml of gentamicin are employed instead of the test blood plasma sample. The $C^{14}O_2$ produced is also measured for each of the controls.

The gaseous $C^{14}O_2$ measurements from these controls are plotted on two-cycle semi-log paper with the log scale as ordinate. The abscissa was divided into 100 units corresponding to the Bactec units, and the gentamicin concentrations constituted the logarithmic ordinate. The points for 0.6, 2.5 and 10 mcg of gentamicin per ml are plotted and connected by two straight lines (i.e., 0.6 point is connected to 2.5 point and 2.5 point is connected to 10 point). The test $C^{14}O_2$ reading is then compared to the graph in order to determine the concentration of gentamicin in the test sample that provides such $C^{14}O_2$ reading.

The following examples are included for illustrative purposes only and are not intended to limit the scope of the invention.

EXAMPLE 1

A culture of gentamicin susceptible *Proteus mirabilis* was grown overnight at 37°C in tryptic soy broth at pH 7.8 and 0.2 ml of the culture was added to test samples and controls in 20 ml serum bottles having rubber septum tops. Each bottle contained 3.0 ml of a medium consisting of 0.2% glucose, 0.1% casein amino acids, 1.0% urea, and tris buffer 0.02M. The medium had a pH of 8.4 and had been filter sterilized.

Control I was formulated by adding 0.2 ml of pooled normal human blood plasma (heparinized) containing 0.6 mcg gentamicin per ml to the medium containing bottles; Control II was formulated by adding 0.2 ml of pooled normal human blood plasma (heparinized) containing 2.5 mcg gentamicin per ml to the medium containing bottles; and Control III was formulated by adding 0.2 ml of pooled normal human blood plasma (heparinized) containing 10 mcg gentamicin per ml to the medium containing bottles. Each of the controls as well as the test sample were replicated.

The test sample was formulated by adding 0.2 ml of the test blood plasma sample to bottles containing the above 3.0 ml of medium.

The contents of each of the bottles were mixed by swirling and then incubated in a water bath at 37°C for 60 minutes. The level of water in the bath was above the level of liquid in the bottles.

Following incubation at 37°C, 1.0 ml of $C^{14}$ urea stabilized with 0.02M sodium azide (1.0 $\mu$Ci/ml) was added to each bottle. The air above the liquid in the bottle containing the stock solution of $C^{14}$ urea was flushed to remove any traces of $C^{14}O_2$ before the $C^{14}$ urea was used. The contents of the bottle were thoroughly mixed by swirling and placed in a 56°C water bath for 15 minutes. Again the level of the water in the bath was above the level of the liquid in the container.

After the incubation at 56°C the bottles were placed in an ice water bath for one minute to cool them. To each bottle 0.2 ml of decyl alcohol (anti-foam agent) was added and the containers were swirled thoroughly. Then 1.0 ml of 2N sulphuric acid (reaction stabilizer) was added and the containers were shaken vigorously. Thereafter the containers were swirled to remove all bubbles. The $C^{14}O_2$ in the gas space of each of the bottles was then measured at room temperature with a Bactec instrument.

Control I provided a reading of 90, Control II provided a reading of 63 and Control III provided a reading of 16. The test sample provided a reading of 73.

The results from the controls were graphed on two-cycle semi-log paper with the log as the ordinate. The abscissa was divided into 100 units corresponding to the Bactec units, and the gentamicin concentrations constituted the logarithmic ordinate. The points for all three controls were plotted and the adjacent points were connected with straight lines. From this graph it was determined that the concentration of gentamicin in the test blood plasma sample was 1.5 mcg/ml.

EXAMPLE 2

A culture of gentamicin susceptible *Proteus mirabilis* was grown overnight in tryptic soy broth at pH 7.8 and at 37°C.

To 20 ml serum bottles having rubber septum tops were added the following: (a) 3.0 ml of a medium consisting of 0.2% glucose, 0.1% casein amino acids, 1.0% urea, and tris buffer 0.02M (medium pH 8.4); (b) 0.2 ml of the *Proteus mirabilis* culture; and (c) 1.0 ml of $C^{14}$ urea in sterile distilled water.

Control I was formulated by adding 0.2 ml of pooled normal human blood plasma (heparinized) containing 0.6 mcg gentamicin per ml to the bottles; Control II was formulated by adding 0.2 ml of pooled normal human blood plasma (heparinized) containing 2.5 mcg gentamicin per ml to the bottles; and Control III was formulated by adding 0.2 ml of pooled normal human blood plasma (heparinized) containing 10 mcg gentamicin per ml to the bottles. Each of the controls as well as the test sample were replicated.

The test sample was formulated by adding 0.2 ml of the test blood plasma sample to bottles containing 3.0 ml of medium 0.2 ml bacterial culture and 1.0 ml $C^{14}$ urea solution.

The contents of each of the bottles was mixed by swirling and then incubated in a water bath at 37°C for 60 minutes. The level of water in the bath was above the level of liquid in the bottles.

After the incubation at 37°C the bottles were placed in an ice water bath for 1 minute to cool them. To each bottle 0.2 ml of decyl alcohol (anti-foam agent) was added and the containers were swirled thoroughly. Then 1.0 ml of 2N sulphuric acid (reaction terminator) was added and the containers were shaken vigorously. Thereafter the containers were swirled to remove all bubbles. The $C^{14}O_2$ in the gas space of each of the bottles was then measured at room temperature with a Bactec instrument.

Control I provided a reading of 85, Control II provided a reading of 75 and Control III provided a reading of 53. The test sample provided a reading of 78.

The results from the controls were graphed on two-cycle semi-log paper with the log scale as the ordinate. The abscissa was divided into 100 units corresponding to the Bactec units, and the gentamicin concentrations constituted the logarithmic ordinate. The points for all three controls were plotted and the adjacent points were connected with straight lines. From this graph it was determined that the concentration of gentamicin in the test blood plasma sample was 1.6 mcg/ml.

Since modifications of this invention will be apparent to those skilled in the art, it is intended that this invention be limited only by the scope of the appended claims.

We claim:

1. A method of determining the level of gentamicin in blood plasma which comprises:
   a. Incubating a viable innoculum of a gentamicin susceptible strain of an adaptive urease producing microorganism for an initial period in an alkaline liquid culture medium containing urea and an aliquot of the liquid portion of blood from a patient being treated with gentamicin;
   b. Adding a measured amount of $C^{14}$ urea to said medium after said initial period of incubation;
   c. Further incubating said culture for a subsequent period in a closed container having a gas space over the alkaline liquid medium at a temperature at which further urease synthesis is interrupted but at which preformed urease activity is enhanced;
   d. Acidifying the medium of step (c) after incubation to terminate further activity;
   e. Determining the amount of $C^{14}O_2$ in the gas space in said container after said subsequent period of incubation; and
   f. Directly comparing said amount of $C^{14}O_2$ with that produced from control media containing an aliquot of pooled normal liquid from human blood and known concentrations of gentamicin processed in the same manner, as specified in steps (a) through (e) above.

2. The method of claim 1 wherein the $C^{14}O_2$ is measured while in the gaseous state by removing at least a portion of the atmosphere from the gas space in said container and transporting it to an ionization chamber.

3. The method of claim 1 wherein the medium after incubation is acidified to a pH not greater than about 2 to terminate further activity.

4. The method of claim 1 wherein $C^{14}O_2$ in the present gaseous space in said container is measured immediately following incubation.

5. The method of claim 1 wherein the microorganism is a strain of the genus Proteus.

6. The method of claim 1 wherein the microorganism is a strain of the species Proteus mirabilis.

7. The method of claim 1 wherein blood plasma is employed.

8. The method of claim 1 wherein blood serum is employed.

9. The method of claim 6 wherein the viable innoculum ranges from about $5 \times 10^6$ to about $5 \times 10^7$ microorganisms, the initial period of incubation is about one hour, and the subsequent period of incubation is about 15 minutes.

* * * * *